（12）United States Patent
Rubner et al.

(10) Patent No.: US 9,044,190 B2
(45) Date of Patent: Jun. 2, 2015

(54) C-ARM COMPUTERIZED TOMOGRAPHY SYSTEM

(75) Inventors: Joseph Rubner, Shoham (IL); Eli Zehavi, Haifa (IL); Leonid Kleyman, Acco (IL); Moshe Shoham, M.p. Hamovil (IL)

(73) Assignee: MAZOR ROBOTICS LTD., Caesarea (IL)

( * ) Notice: Subject to any disclaimer, the term of this patent is extended or adjusted under 35 U.S.C. 154(b) by 1278 days.

(21) Appl. No.: 12/442,689

(22) PCT Filed: Sep. 25, 2007

(86) PCT No.: PCT/IL2007/001193
§ 371 (c)(1),
(2), (4) Date: Jul. 27, 2010

(87) PCT Pub. No.: WO2008/038283
PCT Pub. Date: Apr. 3, 2008

(65) Prior Publication Data
US 2010/0284601 A1    Nov. 11, 2010

Related U.S. Application Data

(60) Provisional application No. 60/846,750, filed on Sep. 25, 2006, provisional application No. 60/907,874, filed on Apr. 20, 2007.

(51) Int. Cl.
*A61B 6/00*    (2006.01)

(52) U.S. Cl.
CPC ............. *A61B 6/4405* (2013.01); *A61B 6/4441* (2013.01)

(58) Field of Classification Search
CPC ............................. A61B 6/4405; A61B 6/4441
USPC ................................................... 378/207, 62
See application file for complete search history.

(56) References Cited

U.S. PATENT DOCUMENTS 5,706,324 A    1/1998    Wiesent et al.
5,951,475 A *  9/1999    Gueziec et al. ............... 600/425
(Continued)

FOREIGN PATENT DOCUMENTS

EP    0917855    5/1999
WO    WO 99/44503 A1    9/1999
(Continued)

OTHER PUBLICATIONS

Extended European search report issued on May 6, 2010, in corresponding European Application No. 07827167.3.
(Continued)

*Primary Examiner* — Allen C. Ho
(74) *Attorney, Agent, or Firm* — Fish & Richardson P.C.

(57) ABSTRACT

A system and method for generating CT-type three dimensional imaging information from a conventional C-arm fluoroscope system. This enables the adaptation of widely used C-arm installations to provide CT-type information. The system uses a three dimensional target disposing in a fixed position relative to the subject, and obtains a sequence of video images of a region of interest of a subject while the C-arm is moved manually or by a scanning motor. Images from the video sequence are analyzed to determine the pose of the C-arm relative to the subject by analysis of the image patterns of the target. Images are selected from the video sequence according to predetermined criteria. A set of two-dimensional image data with associated positional data is obtained, which is used to reconstruct a three dimensional volumetric set of imaging data of the region of interest of the subject.

14 Claims, 3 Drawing Sheets

(56) References Cited

U.S. PATENT DOCUMENTS

| | | | |
|---|---|---|---|
| 5,963,612 A * | 10/1999 | Navab | 378/4 |
| 6,038,282 A | 3/2000 | Wiesent et al. | |
| 6,049,582 A | 4/2000 | Navab | |
| 6,118,845 A * | 9/2000 | Simon et al. | 378/62 |
| 6,243,439 B1 * | 6/2001 | Arai et al. | 378/20 |
| 6,285,739 B1 * | 9/2001 | Rudin et al. | 378/98.8 |
| 6,289,235 B1 * | 9/2001 | Webber et al. | 600/426 |
| 6,359,960 B1 | 3/2002 | Wahl et al. | |
| 6,382,835 B2 * | 5/2002 | Graumann et al. | 378/198 |
| 6,484,049 B1 * | 11/2002 | Seeley et al. | 600/426 |
| 6,585,412 B2 * | 7/2003 | Mitschke | 378/207 |
| 6,662,036 B2 * | 12/2003 | Cosman | 600/411 |
| 6,666,579 B2 * | 12/2003 | Jensen | 378/197 |
| 6,810,278 B2 * | 10/2004 | Webber et al. | 600/407 |
| 6,851,855 B2 * | 2/2005 | Mitschke et al. | 378/207 |
| 6,912,265 B2 * | 6/2005 | Hebecker et al. | 378/4 |
| 6,928,142 B2 * | 8/2005 | Shao et al. | 378/63 |
| 7,048,440 B2 * | 5/2006 | Graumann et al. | 378/197 |
| 7,066,646 B2 * | 6/2006 | Pescatore et al. | 378/207 |
| 7,142,633 B2 | 11/2006 | Eberhard et al. | |
| 7,147,373 B2 * | 12/2006 | Cho et al. | 378/207 |
| 7,186,023 B2 * | 3/2007 | Morita et al. | 378/207 |
| 7,426,256 B2 * | 9/2008 | Rasche et al. | 378/8 |
| 7,671,887 B2 * | 3/2010 | Pescatore et al. | 348/25 |
| 7,712,961 B2 * | 5/2010 | Horndler et al. | 378/207 |
| 7,844,094 B2 * | 11/2010 | Jeung et al. | 382/131 |
| 7,950,849 B2 * | 5/2011 | Claus et al. | 378/207 |
| 8,104,958 B2 * | 1/2012 | Weiser et al. | 378/207 |
| 8,326,403 B2 * | 12/2012 | Pescatore et al. | 600/426 |
| 2002/0122536 A1 | 9/2002 | Kerrien et al. | |
| 2002/0163996 A1 | 11/2002 | Kerrien et al. | |
| 2002/0188194 A1 | 12/2002 | Cosman | |
| 2003/0088179 A1 | 5/2003 | Seeley et al. | |
| 2005/0220264 A1 | 10/2005 | Homegger | |
| 2006/0182216 A1 | 8/2006 | Lauritsch et al. | |

FOREIGN PATENT DOCUMENTS

| | | |
|---|---|---|
| WO | 2004081877 A1 | 9/2004 |
| WO | 2005015125 | 2/2005 |

OTHER PUBLICATIONS

Translation of Chinese Office Action issued on Jun. 2, 2010, in corresponding Chinese Application No. 200780039767.3.

Translation of Japanese Office Action issued on Jul. 3, 2012 in corresponding Japanese Application No. 2009529855.

Translation of Japanese Office Action dated Sep. 3, 2013 in corresponding Japanese Application No. 2009529855.

* cited by examiner

C-ARM COMPUTERIZED TOMOGRAPHY SYSTEM

CROSS REFERENCE TO PRIOR APPLICATIONS

This is the U.S. National Phase application under 35 U.S.C. §371 of International Patent Application No. PCT/IL2007/001193, filed Sep. 25, 2007, and claims the benefit of U.S. Provisional Application No. 60/846,750, filed Sep. 25, 2006 and U.S. Provisional Application No. 60/907,874, filed Apr. 20, 2007, both of which are incorporated by reference herein. The International Application published in English on Apr. 3, 2008 as WO 2008/038283 under PCT Article 21(2).

FIELD OF THE INVENTION

The present invention relates to the field of CT imaging, especially as generated using a conventional C-arm fluoroscopic image system.

BACKGROUND OF THE INVENTION

Computerized Tomography (CT) is generally performed using a dedicated CT system, which is an expensive piece of equipment, found in limited numbers within the health care environment, and generally, because of its size and weight, in dedicated locations within the health care facility. It is very rare to find a CT system located in the operating room, where it would be available for intraoperative imaging. On the other hand, the C-arm type of X-ray fluoroscopic imaging system is a reasonably low cost piece of equipment, very widely found in both hospitals and clinics, and generally sufficiently mobile that it can be moved to the patient at the point of care or in the operating room. A number of prior art publications have described systems for providing three dimensional, CT-type, imaging information, using the two-dimensional imaging data provided by common C-arm systems. Such systems should be able to provide CT-type information using a system only a fraction of the cost of a dedicated CT system. At least one such a system is also available commercially, and it appears to use a motor to slowly rotate the C-arm in a controlled manner, stopping at predetermined incremental positions of the C-arm motion to generate fluoroscopic images.

One such C-arm based CT system is described in European Patent Application for "X-Ray photographing apparatus and method capable of performing computerized tomography using C-arm", published as EP 0917855. This application, while describing some conceptual elements of the aims and advantages of such a system, does not appear to contain essential enabling details. Other such systems are described in U.S. Pat. No. 6,049,582 to N. Navab for "C-arm Calibration Method for 3-D Reconstruction", U.S. Pat. No. 7,142,633 to J. W. Eberhard et al., for "Enhanced X-ray Imaging System and Method", and in US 2006/0182216 to G. Lauritsch et al., for "Method for Reconstructing a CT Image using an Algorithm for a Short-Scan Circle combined with Various Lines". In addition, U.S. Pat. No. 6,038,282, to K. Wiesent et al., describes a method and apparatus for generating in an X-ray C-arm imaging system, a voxel-driven back projection without the calculation of positional coordinates and physical focus and detection positions. U.S. Pat. No. 5,706,324, also to K. Wiesent et al., describes a method and apparatus for the use in a CT system of special marks which are imaged during scanning, and by which the geometry of the image can be determined.

In U.S. Pat. No. 6,666,579 for "Method and Apparatus for Obtaining and Displaying Computed Tomography Images using a Fluoroscopy Imaging System", to V. T. Jensen, there is described a C-arm system which provides CT-type information for diagnostic purposes and interventional procedures. The system includes a C-arm having an x-ray source and a receptor for obtaining fluoroscopic images of a patient. The C-arm is moved through an image acquisition path along which at least first and second images are obtained. An acquisition module obtains multiple 2-D fluoroscopic images at desired positions along the image acquisition path and an image processor constructs a 3-D volume of object data based on the 2-D fluoroscopic images. Patient information is displayed based upon the 3-D volume of patient information. A position tracking system is included to track the position of the receptor, patient and (if included) a surgical instrument. The position information is used to control the time at which exposures are obtained and (if included) to superimpose instrument graphical information on a display with patient information.

However, this system appears to be a dedicated system, including a number of additional accessory components not generally found in the common C-arm fluoroscope imager, in particular, the tracking system required to define the positions of the source, subject, detector and surgical tool if present. Although considerably less costly than a CT system, this system does involve the capital expenditure of the new equipment, or the cost of amending an existing C-arm fluoroscope by installation of the additional features required for its operation.

There therefore exists a need for a system for obtaining CT-type information from the outputs of conventional existing, C-arm fluoroscopic imaging systems, by means of simple software routines, without the need to make any changes or additions to the structure of the existing C-arm fluoroscope, thus overcoming at least some of the disadvantages of prior art systems and methods.

The disclosures of each of the publications mentioned in this section and in other sections of the specification are hereby incorporated by reference, each in its entirety.

SUMMARY OF THE INVENTION

The present invention seeks to provide a new system and method for generating three dimensional CT-type information from a conventional C-arm fluoroscope imaging system which provides two-dimensional images. This enables the adaptation of widely used C-arm installations to provide CT-type information. The system preferably utilizes in a novel manner features generally present on a conventional C-arm system, and does not involve any changes or additions to the structure of the C-arm system, such that the invention can be implemented using existing C-arm installations, even of the simplest type.

The system uses a three dimensional target disposed in a fixed position relative to the subject, and obtains a sequence of video images of a region of interest of a subject while the C-arm is moved around the subject either manually or, for those systems where provided, by a motor. No assumptions are made regarding the centricity of the C-arm or the relative position of the patient, as long as the region of interest appears in the video sequence, or at least in the majority of the frames of the video sequence.

Each of the images is analyzed to determine the pose of the C-arm relative to the subject by analysis of the image patterns of the target. Images are then selected, according to criteria described hereinbelow, to provide the imaged data of the region of interest of the subject. Alternatively and preferably, a number of frames from the video sequence, or a number of fields in the case of interlaced video, are selected and analyzed to determine the pose of the C-arm relative to the subject by analysis of the image patterns of the target. According to either of these methods, a series of two-dimensional image data with associated positional data is obtained, which is used to reconstruct a three dimensional volumetric set of imaging data of the region of interest of the subject.

The system preferably utilizes one or more of the following features:

(a) Video data obtained from the C-arm imaging system is utilized to provide a sequence of two-dimensional X-ray images from which the data processing software generates the three dimensional CT information. Video representation of the imaged data is usually available on prior art C-arms, but its use has generally been limited to enabling the doctor to perform dynamic visual observation of the region of interest being imaged. Conventional C-arms commonly output the video as an analog video sequence, using standard formats such as PAL and NTSC. According to preferred embodiments of the present invention, the use of continuous video imaging enables the data acquisition process to be significantly faster than with prior art C-arm imaging systems, since the C-arm does not need to be stopped to acquire every image. Since the use of continuous video may introduce motion blur, and may involve other artifacts (such as interlacing when analog video is used), image processing algorithms, including deblurring techniques, are used to enable such continuous image acquisition "on the fly". Another advantage of using video data is the availability of a large number of images, all of which are available for the reconstruction.

(b) Motion of the C-arm can preferably be performed either by means of a built-in motion system, or by simple manual movement, which need not be uniform.

(c) The pose of the C-arm relative to the subject is determined by the use of a three dimensional target, incorporating a three dimensional array of X-ray opaque marker points, which will be visible on the fluoroscope images. The target is disposed in a position close to or on the subject, such that at least a part of the image of the target is seen in the fluoroscope images. The target must be affixed, either to the subject or to the operating table or bed on which the subject is fixed, so that its position is unchanged relative to the subject, though its absolute position relative to the subject need not be known. The target image information is processed using a conventional algorithm used for this purpose, to determine the angular and translational position of the C-arm at any point in time, such that the system software can thus determine the position and orientation of the subject within the imaged data of each frame. The target is preferably tracked along the video sequence using a dynamic model in order to increase accuracy, speed, and robustness of the pose estimation.

(d) This dynamic model may preferably be used to compare the image data obtained in successive frames, thus enabling the prediction of the expected position of the target plate in successive frames, such that the actual target image can be acquired more rapidly and the pose thus determined more rapidly. Additionally, the dynamic model enables corrections to be made to the image data for missing or deviant details, such that the image data can be improved. Furthermore, the use of the dynamic model enables the C-arm dewarping function to be performed more efficiently. Dewarping is a calibration procedure performed to correct distortions of the images. It is achieved by affixing a phantom with marker balls having predefined positions to the image intensifier, and solving the dewarping function to eliminate any distortion in the image of these balls. Using the dynamic model makes it unnecessary to perform the complete dewarping calculation for every frame, since reliance can be made on one initial full calculation, and the parameters for successive frames updated according to the change in the dewarping phantom image. Additionally, the dynamic model may preferably be used to select images for use according to their quality, rejecting or correcting images having degraded features.

(e) The output data from the sequence of video frames grabbed by the system software is processed by means of a reconstruction engine to generate CT-type data, enabling three-dimensional images of the region of interest to be constructed.

By the above means, using the preferred methods and algorithms described herewithin for processing the acquired 2-dimensional image data, CT-type 3-dimensional data may be obtained from an existing conventional C-arm fluoroscope, without the need for any physical adaptations to the system.

Though the present invention has been described as being suitable for use with an existing C-arm system, this being a particular advantageous aspect thereof, it is to be understood that the invention is also meant to cover a dedicated C-arm system constructed to use the methods and parts described herein.

There is therefore provided in accordance with a preferred embodiment of the present invention, a an imaging apparatus, comprising:

(i) an X-ray source, (ii) an X-ray camera connected to the source by a movable C-arm, the X-ray camera generating a sequence of video images of a region of interest of a subject disposed between the source and the camera, (iii) a target comprising an array of X-ray opaque markers in a three dimensional pattern, the target being disposed in a fixed position relative to the subject such that at least part of the target is imaged in at least part of the sequence of video images, (iv) an image processing unit determining the pose of the C-arm relative to the subject for at least some of the video images, by analyzing image patterns of the target, and (v) a reconstruction engine calculating from selected video images and their determined poses, a three-dimensional volumetric set of imaging data of the region of interest of the subject.

In the above described system, the image processing unit may either preferably determine the pose of the C-arm relative to the subject for essentially all of the video images, before selection of any video images, or it may determine the pose of the C-arm relative to the subject only for selected ones of the video images. Each of the video images may preferably be either a video frame, or at least some of the video images may be interlaced fields of an analog video frame.

In accordance with still another preferred embodiment of the present invention, the image processing unit may preferably comprise an image deblurring module for reducing the effect of motion of the C-arm. In any of the above described systems, the C-arm may be adapted to be moved manually, or to be motor driven. Additionally, the target may preferably be affixed to the subject or to a platform on which the subject is lying, such as the OP bed.

There is even further provided in accordance with a preferred embodiment of the present invention, an imaging apparatus as described above, and wherein the image processing unit comprises an image sequence comparison module, which predicts features of a selected video image by analysis of at least some images preceding the selected image. The predicted features may preferably be the expected positions of the image patterns of the target, such that calculation of the pose associated with the selected image can be performed without the need to search for the image patterns of the target over the whole of the selected image. Alternatively and preferably, the predicted features may be expected features missing from the selected video image. Furthermore, the image sequence comparison module preferably predicts a dewarping function for the pose associated with the selected video image, by analysis of the dewarping function of the pose associated with at least some images preceding the selected image.

There is also provided in accordance with a further preferred embodiment of the present invention a method of generating a volumetric set of imaging data, comprising the steps of:

(i) providing an X-ray imaging system having a source and a camera connected by a C-arm, the system imaging a region of interest of a subject disposed between the source and the camera, (ii) disposing a target having a series of X-ray opaque markers disposed in a three dimensional pattern, in a fixed position relative to the subject, and where at least part of it will be imaged by the imaging system, (iii) applying a motion path to the C-arm, (iv) obtaining from the camera a sequence of video images of the region of interest of the subject while the C-arm performs the motion path, (v) determining the pose of the C-arm relative to the subject for at least some of the sequence of video images by analyzing the image patterns of the target, (vi) selecting a number of images from the video sequence, and (vii) using the selected video images and their determined poses to reconstruct a three-dimensional volumetric set of imaging data of the region of interest of the subject.

In the above described method, the pose of the C-arm relative to the subject may preferably be determined either for essentially all of the video images, before selection of any video images, or alternatively, only for selected ones of the video images. Each of the video images may preferably be either a video frame, or at least some of the video images may be interlaced fields of an analog video frame.

In accordance with still another preferred embodiment of the present invention, the above mentioned method may preferably further comprise the step of processing the images in a deblurring module for reducing the effect of motion of the C-arm. In any of the above described methods, the step of applying a motion path to the C-arm may be performed manually or by means of a motor. Additionally, the target may preferably be affixed to the subject, or to a platform on which the subject is lying, such as the OR bed.

There is even further provided in accordance with a preferred embodiment of the present invention, a method as described above, and further comprising the step of processing the images in an image sequence comparison module, which predicts features of a selected video image by analysis of at least some images preceding the selected image. The predicted features may preferably be the expected positions of the image patterns of the target, such that calculation of the pose associated with the selected image can be performed without the need to search for the image patterns of the target over the whole of the selected image. Alternatively and preferably, the predicted features may be expected features missing from the selected video image. Furthermore, the image sequence comparison module preferably predict a dewarping function for the pose associated with the selected video image, by analysis of the dewarping function of the pose associated with at least some images preceding the selected image.

BRIEF DESCRIPTION OF THE DRAWINGS

The present invention will be understood and appreciated more fully from the following detailed description, taken in conjunction with the drawings in which.

DETAILED DESCRIPTION OF PREFERRED EMBODIMENTS

Figure 1:
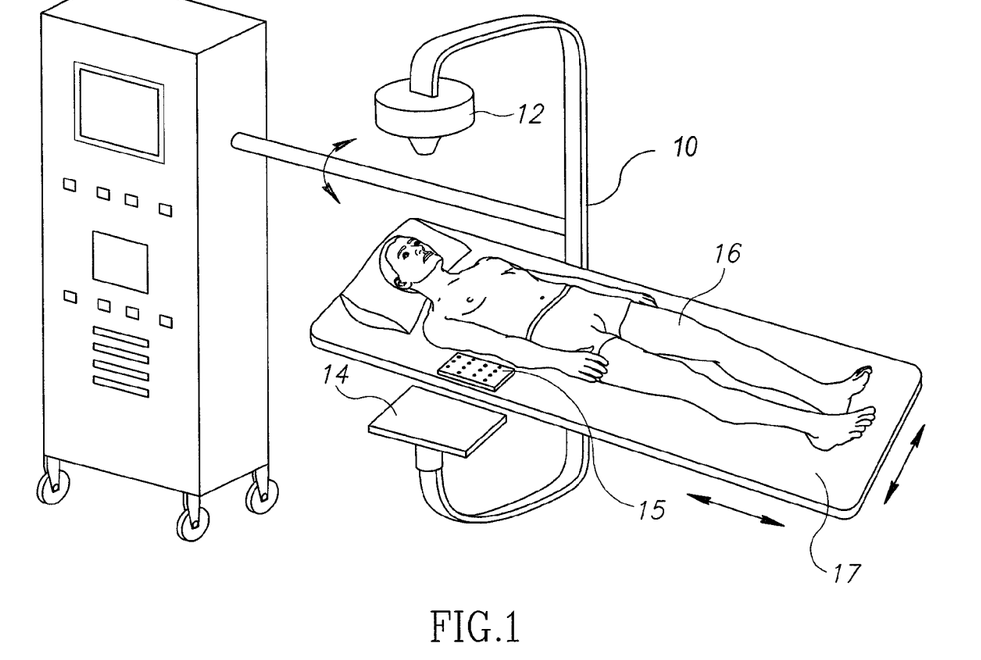
FIG. 1 shows schematically a C-arm system, constructed and operative according to a preferred embodiment of the present invention, enabling generation of 3-dimensional CT-type information.

Reference is now made to FIG. 1, which illustrates schematically a C-arm system, constructed and operative according to a preferred embodiment of the present invention, which enables the generation of 3-dimensional CT-type information generally using the existing features of the C-arm, without the need for structural changes. The C-arm 10 has an X-ray source 12 on one end of its jaws, and a detector array 14 at the other end, for detecting the two-dimensional absorption image generated by passage of the X-rays through the subject 16 lying on the bed 17. The detector array preferably comprises an image intensifier coupled to a video camera, thus converting the incident photons into a video signal which dynamically shows the X-ray absorption shadow images.

Figure 2:
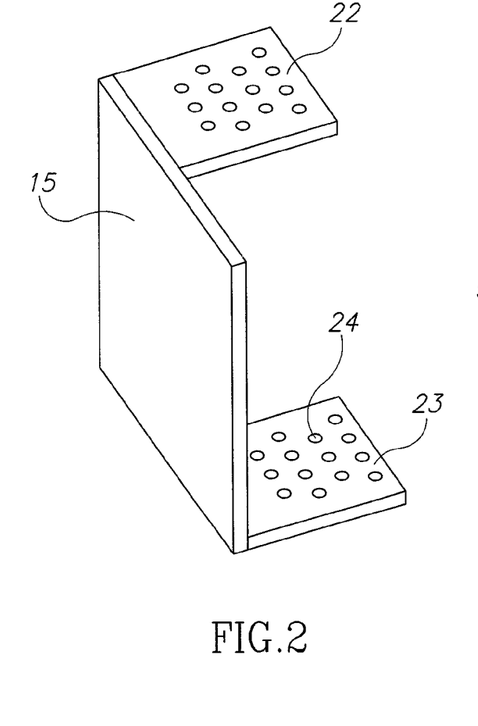
FIG. 2 is a schematic drawing of an example of a three dimensional target plate for use in the C-arm system of FIG. 1.

A three dimensional target 15 containing X-ray opaque marker balls, is located in a fixed position relative to the subject, so that its image, or at least part of it, shows up in the video images generated by the system. The target can preferably be attached to the bed on which the subject is lying, or attached to or placed on the subject him/herself. The actual position does not need to be defined so long as that position remains fixed during the complete scan. Such three dimensional plates are known in the art, both as target plates for determining the source position by use of a projection grid, and, when located on or close to the detector array, as phantoms for performing the dewarping function in a conventional C-arm system. In the present invention, an adaptation of the former function is used, to enable the 3-D pose of the acquired fluoroscopic images to be determined relative to the target position, and hence, relative to the subject. This target, or at least part of it, can be identified in each of the two dimensional frames taken from the video sequence, and from the known three-dimensional arrangement of its X-ray opaque marker balls, the pose of the X-ray source relative to the subject may be determined, preferably for each image of the video sequence. In practice, in order to save computing time, the pose of the imaging system relative to the subject is only preferably determined for those images used ultimately in the reconstruction of the 3-dimensional CT-type data set. Such a target can take a number of alternative forms. One schematic example of such a target plate is shown in FIG. 2. The plate preferably contains two separated planes 22, 23 containing radio-opaque fiduciary marker balls 24, with a known geometric relationship between the two planes.

The target plate should preferably be easily visible in all of the image frames taken along the path of the C-arm. This may be a difficult task, since the patient, and hence the target will not generally be located in a position concentric with the center of rotation of the C-arm, and it may therefore be difficult to ensure that both the subject and the target are in-frame in all of the frames recorded. According to another preferred embodiment, the target plate has lateral dimensions of sufficient size that every frame shows at least a part of the target for pose estimation. Such use of only part of the target is possible according to this embodiment of the present invention, because the video sequence enables comparison of the position of markers in that part of the target seen in one frame, with at least some of the same markers in that part of the target seen in one or more previous frames, or with at least some of the same markers in larger parts of the target in previous frames, or even with at least some of the same markers in the whole target in previous frames. Such a continuous comparison process with previously captured frames means that the part of the target used for determining the pose at any time may move over the target during the course of the C-arm motion. Alternatively and preferably, the target could be constructed using a pattern form which repeats itself over the whole target, or a pattern positionally coded so that the location of each region within the target is known, such that even separate parts of the complete target could function independently to define the pose, besides the positional tracking comparison described previously in this paragraph.

In use, the target plate is set in a position which is fixed relative to the region of interest of the subject, either by affixing directly to the subject, or by affixing to the bed or operating table on which the subject is fixed. According to a further preferred embodiment of the present invention, the target could be in the form of a semi-flexible three dimensionally structured surface, which can be draped over any part of the subject or the bed, but which, once deployed, maintains its position relative to the subject being imaged.

The X-ray source is rotated over the region of interest, either by moving the C-arm manually, or by use of a built-in drive system. Any preferred motion path can be used, such as a simple arcuate motion, or a combination of a circular motion with successive lateral motions along the length of the subject's region of interest, or transversely across the width of the region of interest, or a wig-wag motion. The motion need not be at a uniform rate, but can, for instance be varied at any desired or convenient rate. Motion can even be stopped temporarily at any point without interfering with the collection of the ultimately required data. As the source traverses the region of interest, a video sequence of X-ray shadow images of the intervening body mass between the X-ray source and the detector array is obtained. Impressed on each of the frames of this video sequence is an image of the three dimensional target, or of at least part of it where a large area target is used. A frame grabber is preferably used to capture individual images from the continuous video. In the processing stage, the image processing algorithm can select individual images from the video sequence, at a rate which is dependent on one or more factors.

Some of the initial factors which may determine which individual images are selected, and how often or how widely spaced, preferably include:

(i) the image resolution and accuracy desired, since the higher the required resolution or accuracy, the more closely spaced the images should be;

(ii) the instantaneous speed of motion of the C-arm, since the slower the sweeping speed, the less frequent is the need for selecting images from the video sequence. On the other hand, the faster the sweeping speed, the more motion blur exists in the images and more total images will be needed;

(iii) deviation from the motion path. By tracking the motion of the c-arm, images with pose that deviates from the motion path can be filtered out as outliers. In addition, frames in which the C-arm moved at a lower speed than that of neighboring frames are preferably selected, again, in order to reduce the motion blur.

(iv) the overall dimensions of the region of interest, since the larger the region to be imaged, the presumed less need for high resolution, and hence the more spaced the images can be.

The speed of the C-arm is not fundamentally limited by the resolution, since even at high scan speeds, there are sufficient frames to ensure an adequate supply of imaging data. For instance, if the acquisition time is 20 seconds with 30 frames/ sec, 600 frames are generated. The only problem with such fast scans is that the frames might be blurred, as mentioned above.

It is to be understood that the invention is not meant to be limited by these suggested preferred limitations, but that any other relevant factor can be used for determining how often or how spatially spaced (for images selected on the basis of spatial or angular separation) the selected images should be.

Additionally, as described more fully hereinbelow, the use according to another preferred embodiment of the present invention, of a dynamic model for the imaging acquisition process, enables the selection procedure to be adjusted in real time in accordance with the actual quality of the images generated by the fluoroscope.

Computer vision (3-D image processing) is then preferably performed to analyze the images of the three dimensional target plate in order to determine the pose of the X-ray source relative to the subject, and then, using this data together with the two dimensional image data derived from each selected frame, in order to generate the data set for inputting to the three-dimensional information reconstruction engine. The reconstruction engine takes the selected set of two dimensional images together with the calculated pose for each image, and generates therefrom a three-dimensional volumetric data set, from which images representing slices of the subject's body in any desired view can be displayed for presentation to the doctor. The algorithms used to reconstruct the volume can be any of the suitable algorithms known in the art, such as the ART/SART techniques, and others.

One of the novel attributes of this preferred mode of operation of the invention is, therefore, that there is no need for more than a three-dimensional target plate and suitable image data processing software in order to generate three-dimensional CT-type data from a conventional, existing C-arm fluoroscope imager.

The use of the above described dynamic system for the C-arm motion tracking, enabled only because of the provision of the sequence of images from the video data, brings a number of operative advantages to the present invention. Firstly, the need to search for and identify the target image at every selected image position of the C-arm is obviated, since the image processing software of the system can be designed to look for the target plate image in its predicted location, which can be known to within a few pixels, based on the knowledge of the previous frame history, instead of having to search for the target plate image over the whole frame. This improves system performance, since the picture analysis time is shortened. This prediction of the target position can even be extended to predicting the approximate position of the individual marker balls, such that the target search procedure becomes even faster and more robust, as the procedure is commenced close to the global optimum.

Similarly, the dynamic system technique enables the C-arm dewarping procedure to be simplified, since instead of calculating the dewarping function separately for every frame, it is generally sufficient to execute a full calculation only for the first frame used, and then to track the dewarping parameters using the dynamic information available from the system. In this way, the dewarping parameters are predicted from the previous frames using the dynamic model and slightly corrected according to the current frame. This allows for more efficient computation of the dewarping function and results in a more smooth, precise and robust function.

Thirdly, the dynamic system method adds robustness to the method, since if for certain C-arm positions, some of the markers of the target plate are occluded or unclear, such as can occur for instance when bony structures of the subject obscure them, the missing or unclear marker positions can be interpolated from data regarding their positions in adjacent frames, both previous to and after those containing the deficient data.

Furthermore, the acquisition of a video sequence of images enables the accuracy of the images to be improved, since frame selection can be made in accordance with the quality of the frame data. Thus, frames where the detail is substandard, for instance, because of an abrupt jump in the C-arm motion, can be avoided for use in reconstructing the 3-dimensional CT-type data. Additionally, since a continuous sequence enables prediction of certain detail to be made, if that detail is not found in its expected position in some of the frames used, for instance due to an unclear or noisy image, then those frames showing the deviant detail can be either rejected as being outliers, or more advantageously, can be corrected by the signal processing software to improve their quality, and their contribution used as part of the desired data set.

The video sequence also allows correction of the determined pose for each frame, if required. Since, notwithstanding intended motion breaks, the motion of the C-arm is assumed to be continuous, at least on a short time scale, the pose of each successive frame can be predicted, and if the target analysis for any frame or frames indicates an abnormal pose, then the supposed correct pose as determined from an interpolation of the poses determined from adjacent frames, can be used to correct the errant pose.

Additionally, the use of blur reduction directional filter techniques in the image processing software enables corrections to be made for overly fast C-arm motion. Although blur reduction filtering is known in the video arts, the technique used in the present invention can be more successful than in the standard video blur reduction routines, since the dynamic modeling used in the present invention provides good knowledge of the direction and speed of motion between successive frames, thus enabling an improved level of blur reduction.

Combination of all of the above features makes the video-based data acquisition more accurate than prior art C-arm CT-type systems, where discrete imaging is performed from only a comparatively small number of orientations.

One problem that arises from the use of the raw video information from an existing C-arm fluoroscope system is that the video is generally output in one of the analog video standards, with interlacing, to make it compatible with TV standards and for display on TV monitors. When used for normal video display, such interlacing does not present any problem. However, in the present invention, since positional data is extracted from the video frames, there will be a meaningful difference between the odd and the even fields of the interlaced frame, since they will be taken at different points of the C-arm motion. Thus, not only will an edge of a feature appear- to be at different points between two interlaced fields, but even the position of the image itself, as determined by the target analysis, will be different. One solution of this problem could be to deinterlace the frames before use is made of the video sequence. Since deinterlacing generally degrades the quality of the image, as an alternative technique, the video processing software used in the present invention is adapted to treat each field of the interlaced frames separately, as if each were sequential. By this manner, the positional data regarding the pose of the field can be accurately computed for each field separately, and in the reconstruction phase, only the relevant lines of the field are used for the reconstruction, together with the field's three dimensional pose. Since both interlaced and uninterlaced video forms can be used in the present invention, it is to be understood the terms frame as used in this application, and as claimed, is meant to include also the fields of an interlaced video, even when not so stated specifically, such that the application is not meant to be limited to either of frames or fields for acquiring the image data.

Figure 3:
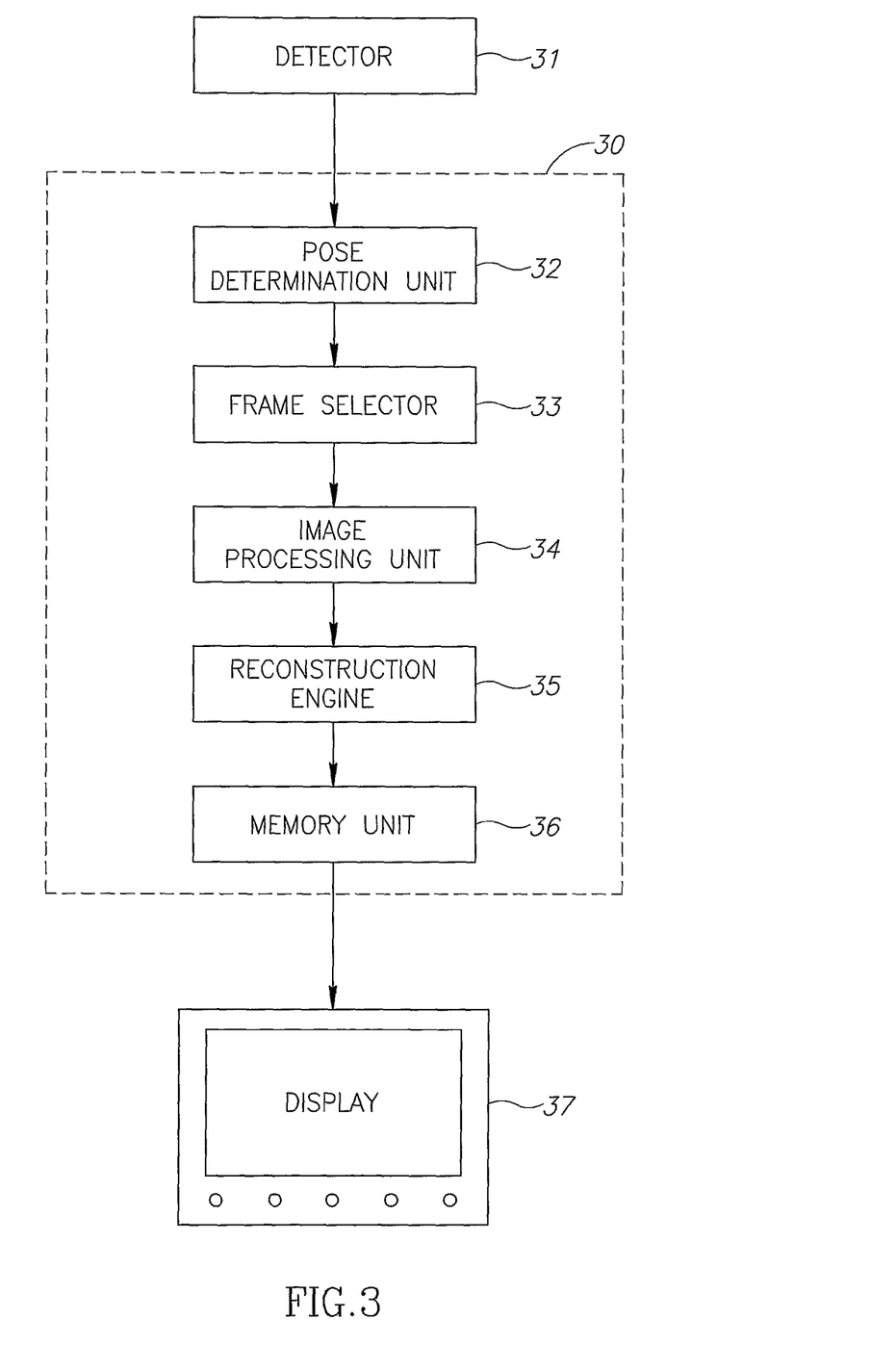
FIG. 3 is a schematic block diagram of the component parts of the C-arm based CT system of FIG. 1.

Reference is now made to FIG. 3, which is a schematic block diagram of the component parts of the C-arm based CT system, showing the main functional units of the image processing module 30 of the system. The system shown in FIG. 3 is a preferred embodiment in which the pose of every frame or filed is determined before any image selection is performed. The detector array 31, generally an image intensifier or a flat panel detector, sends its output signals to a pose determination unit, 32, which looks for the target in the frame (or field), and from the position of the marker balls therein, determines the pose of the X-ray source relative to the subject at that frame. Within the software of the image processing module 30, a frame selector 33 operates to select frames from the video sequence. Frames are selected according to any of the criteria mentioned hereinabove, whether related to angular pose, scan speed, or any other suitable criterion. Although this unit is described as a "frame selector", this term is to be understood to include the functional unit for those embodiments where separate fields of the frame are processed. For each of the selected frames (or fields of a frame), the image processing unit 34 that follows the frame selector, processes only the selected images—typically dewarping and normalizing them. Using the two dimensional image data derived from the selected frames, together with the pose information previously obtained for each selected frame, the image processing unit 34 then generates the data set for inputting to the three-dimensional information reconstruction engine 35. The image processing unit 34 also preferably incorporates an image sequence comparison module (not shown), for predicting features of a selected image by analysis of the content of the preceding image or images and/or the successive image or images, so that the missing feature image improvement operation, and the dewarping function prediction operation can be performed. Additionally, the image processing unit 34 also preferably incorporates an image debluring unit, for reducing the effect of C-arm motion on the image data. The output of the reconstruction engine 35 is transferred to the system memory 36, from where it can be withdrawn for display 37 to the doctor of any desired image slice of the subject or a three dimensional image, as is known in conventional CT imaging technology. In addition, the reconstructed volume can be passed on to other devices for further processing or analyzing, e.g. by using the DICOM format.

According to other preferred embodiments of the present invention, image selection can be performed on a basis other than the position of the scan, such that the pose determination does not have to be performed for every frame/field before the frame selection. In such an embodiment, it is to be understood that the frame selector 33 of FIG. 3, with its selection criteria accordingly adjusted for such an embodiment, would come before the pose determining unit 32.

Figure 4:
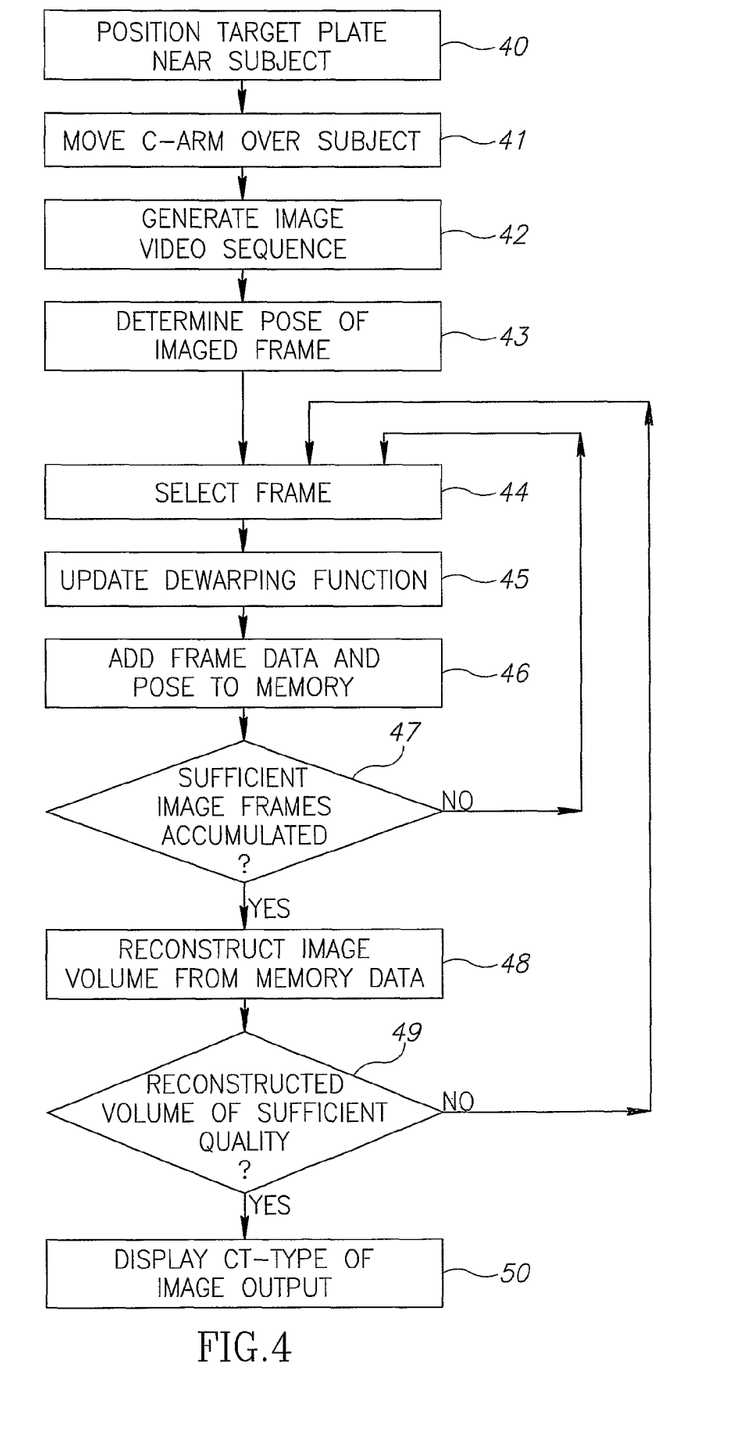
FIG. 4 is a schematic flow chart of a method, according to a preferred embodiment of the present invention, by which the C-arm based CT imager operates to generate its output images.

Reference is now made to FIG. 4, which is a schematic flow chart of a method according to a preferred embodiment of the present invention, by which the C-arm based CT imager operates to generate its output volume. The flow chart shows only those preferred steps specific to the methods of the present invention. As with all C-arm imaging procedures, before implementing the various steps of the method of the present invention shown in FIG. 4, a dewarping phantom is affixed to the c-arm and a clear image in taken. The calibration information is used to track the phantom balls and to dewarp and normalize the image. At step 40, the three dimensional target is fixed in place relative to the subject to be imaged. The C-arm is then moved in step 41 in its desired path over the region of interest of the subject, during which time, in step 42, a video sequence of images is captured. In step 43, the frames are processed in the image processing module 30 of FIG. 3, in order to extract the image data and its associated pose. From this sequence of images, selection of frames is made in step 44. The frames are most conveniently selected based on their angular coverage, for instance, selection of a frame is performed at regular angular intervals, such as every 1 degree. However, frames may also be selected according to the criteria described hereinabove. In step 45, the dewarping function determined in the frame previous to that currently selected is updated using the data obtained from the phantom image in the currently selected frame, and the selected frames are dewarped and normalized. This data is passed in step 46 to the system memory unit, where it is stored together with the remainder of the accumulated two dimensional data. A decision is made in step 47, as to whether sufficient frames and their pose have been accumulated in order to provide data of a quantity and quality required to generate volumetric data set useful for outputting CT-type information. If insufficient data has been accumulated, the decision is made to select more video image frames in step 44. When sufficient data has been accumulated, or when the C-arm has reached the end of its travel, or when the operator has signaled the end of the scan, the data is passed to the reconstruction engine, where it is transformed in step 48 into a volumetric data set suitable for outputting CT-type three dimensional images. The volumetric data generated in the reconstruction engine 35 in step 48 is analyzed for quality and sufficiency, and if required, for example if it is found that there is not enough information from a specific direction for good reconstruction, additional frames may be requested in step 49 from the frame selector 33 as the reconstruction progresses. Finally, in step 50, the volumetric data is displayed according to the attending doctor's request.

For those embodiments where the frame selection procedure is performed before the pose determination analysis, the order of the flow chart steps will be amended accordingly.

Standard C-arm systems generally use an automatic intensity contrast/brightness control, by modifying the voltage and current of the source to adjust for variations in opacity of the object being imaged. This is done in order to obtain images of similar overall brightness levels. The systems typically use the total integrated intensity of the image to adjust the source intensity parameters.

Intensity changes can change the apparent size of an object being imaged, since, for example, a higher intensity incident beam will more easily penetrate and traverse the outer edges of an opaque object such as a bone, making the outer edges appear more transparent, and making the bone appear correspondingly narrower. Intensity changes can thus change the actual appearance of an object such that the same object will have different intensity in different frames. As the 3D reconstruction process is based on the uniformity of the image intensity as a function of the object density, the images needs to be normalized to common parameters.

Therefore, in order to normalize the size of features on each image in spite of changes in the intensity of the illumination, it is necessary to monitor the intensity level of the source.

Figure 5:
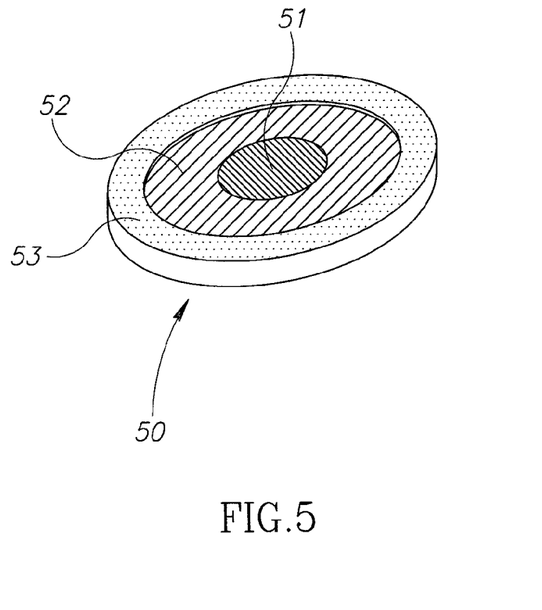
FIG. 5 is a schematic view of a novel intensity sensor or target, constructed and operative according to a further preferred embodiment of the present invention.

Reference is now made to FIG. 5, which is a novel intensity sensor or target 50, constructed and operative according to a further preferred embodiment of the present invention. The sensor is constructed of at least three regions having different known absorptivity to the X-radiation. In the embodiment shown in FIG. 5, three regions are shown 51, 52, 53, arranged as concentric circular areas, but there is generally no limitation as to the shape of the regions, so long as all three regions can be readily imaged in the fluoroscope. The ratio between the absorptivities is known, and between the 3 regions, there are thus 2 known ratios. The individual grey levels of the regions are a function of the intensity, but the ratios are fixed. By measuring the intensities at the different regions and by using Beer's law:

$$I = I_0 e^{-\int \mu(x) ds}$$

it is possible to solve for $I_0$.

Often, the intensity target will be located on top of a material other than air. In such case, Beer's equation has a new unknown, $\alpha$, representing the effect of that material:

$$I = I_0 e^{-\int \mu(x) ds - \alpha}$$

As we have at least 3 regions, we are able to solve for both $I_0$ and $\alpha$.

In order to make this normalization more robust, and to account for cases where intensity targets are on top of several different materials, it is preferable to use several such targets around the image and possibly, targets with more than 3 regions.

The invention has been described and claimed in terms of the commonly known C-arm system. It is to be understood though, that the term C-arm is not meant to be limited to systems having specifically C-shaped arms, but is rather used generically to include any X-ray imaging system which generates two-dimensional images from source and detector units which move around the subject being imaged, with a fixed relationship to each other.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

We claim:

1. A method of using a C-arm X-ray fluoroscopic two dimensional imaging system for generating a volumetric set of imaging data, comprising the steps of:

providing an X-ray fluoroscopic two dimensional imaging system having a source and a camera connected by a C-arm, said system imaging a region of interest of a subject disposed between said source and said camera;

disposing a target having a series of X-ray opaque markers disposed in a three dimensional pattern, in a fixed position relative to the subject, and where at least part of the target will be imaged by said X-ray imaging system;

manually applying a motion path to said C-arm;

obtaining from said camera a sequence of video images of said region of interest of the subject while said C-arm performs said motion path;

determining a pose of said C-arm relative to the subject for at least some of said sequence of video images by analyzing image patterns of said target;

selecting a number of video images from said sequence of video images; and using said selected video images and their determined poses to reconstruct a three-dimensional volumetric set of imaging data of said region of interest of the subject.

2. A method according to claim 1, wherein said pose of said C-arm relative to the subject is determined for essentially all of said video images, before selection of any video images.

3. A method according to claim 1, wherein said pose of said C-arm relative to the subject is determined only for selected ones of said video images.

4. A method according to claim 1, wherein at least some of said sequence of video images are interlaced fields of an analog video frame.

5. A method according to claim 1, further comprising the step of processing said selected video images in a deblurring module for reducing the effect of motion of said C-arm.

6. A method according to claim 1, wherein said disposing of said target in a fixed position relative to the subject is achieved by affixing said target to any of the subject, or a bed or a table on which the subject is lying.

7. A method according to claim 1, further comprising the step of processing said selected video images in an image sequence comparison module, which predicts features of a selected video image by analysis of at least some video images preceding said selected video image.

8. A method according to claim 7, wherein said predicted features are the expected positions of the image patterns of said target, such that calculation of the pose associated with said selected image can be performed without the need to search for said image patterns of said target over the whole of said selected image.

9. A method according to claim 7, wherein said predicted features are expected features missing from said selected video image.

10. A method according to claim 7, wherein said image sequence comparison module predicts a dewarping function for the pose associated with said selected video image, by analysis of the dewarping function of the pose associated with at least some images preceding said selected image.

11. A method according to claim 1, wherein said C-arm motion path is not isocentric.

12. A method according to claim 1, wherein said C-arm motion path is non-uniform.

13. A method according to claim 1, wherein said motion path can be arbitrarily selected.

14. A method according to claim 1, wherein motion of said C-arm can be stopped temporarily during its path.

* * * * *